(12) United States Patent
Kondo et al.

(10) Patent No.: US 6,504,900 B2
(45) Date of Patent: Jan. 7, 2003

(54) OPTICAL SAMPLE X-RAY TESTING APPARATUS AND METHOD FOR TESTING OPTICAL SAMPLE WITH X-RAYS

(75) Inventors: Hiroyuki Kondo, Tokyo (JP); Masayuki Shiraishi, Tokyo (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/814,729

(22) Filed: Mar. 23, 2001

(65) Prior Publication Data

US 2002/0003858 A1 Jan. 10, 2002

(30) Foreign Application Priority Data

Mar. 24, 2000 (JP) ........................................ 2000-083398

(51) Int. Cl.[7] .............................................. G01N 23/20
(52) U.S. Cl. ............................. 378/70; 378/84; 378/88; 378/34; 378/43
(58) Field of Search ............................. 378/84, 70, 79, 378/88, 206, 205, 34, 43, 145, 147, 78; 250/492.1

(56) References Cited

U.S. PATENT DOCUMENTS 5,153,898 A * 10/1992 Suzuki et al. ................. 378/34
5,204,887 A * 4/1993 Hayashida et al. .......... 378/145
5,249,215 A * 9/1993 Shimano ................... 250/492.1
5,517,546 A * 5/1996 Schmidt ....................... 378/205
5,848,119 A * 12/1998 Miyake et al. ................ 378/34
6,041,098 A * 3/2000 Touryanski et al. ........... 378/70

FOREIGN PATENT DOCUMENTS

JP           4-128641         4/1992
JP          10-318945        12/1998

* cited by examiner

Primary Examiner—Robert H. Kim
Assistant Examiner—George Wang
(74) Attorney, Agent, or Firm—Oblon, Spivak, McClelland, Maier & Neustadt, P.C.

(57) ABSTRACT

An optical sample X-ray testing apparatus including an X-ray source which is configured to radiate X-rays including a group of line spectra. At least one line spectrum selecting device is provided between the X-ray source and an optical sample and configured to direct substantially one line spectrum among the group of line spectra from the X-ray source toward the optical sample. An optical characteristics finding device is configured to find optical characteristics of the optical sample based on radiation of the substantially one line spectrum through the line spectrum selecting device onto the optical sample.

31 Claims, 6 Drawing Sheets

OPTICAL SAMPLE X-RAY TESTING APPARATUS AND METHOD FOR TESTING OPTICAL SAMPLE WITH X-RAYS

CROSS-REFERENCE TO RELATED APPLICATIONS

The present application claims priority to Japanese Patent Application No. 2000-083398, filed Mar. 24, 2000, entitled "X-ray Sample Testing Apparatus". The contents of that application are incorporated herein by reference in their entirety.

BACKGROUND OF THE INVENTION

1. Field of the Invention

The present invention relates to an optical sample X-ray testing apparatus and a method for testing an optical sample with X-rays. Further, the present invention relates to a method for manufacturing a reflective mask blank configured to be exposed with X-rays and a method for manufacturing a mirror configured to be used in an X-ray optical system.

2. Discussion of the Background

Recently, semiconductor manufacturing techniques are rapidly becoming more detailed and thus the analysis and observation of semiconductor regions are increasingly miniaturized. Along with such a trend, use of X-ray has been increasing in the area of, for example, X-ray optical devices such as X-ray exposure devices, X-ray microscopes and X-ray analyzers. To manufacture these devices, the use of X-ray optical elements such as multi-layered film mirrors, oblique-incidence mirrors, filters, beam splitters is necessary. A key to manufacture a high performance X-ray optical device is how to manufacture optical elements having good optical properties such as reflectivity, transmittance and degree of scattering. In order to make an optical element capable of high performance, an optical element is evaluated by using an X-ray beam having a wavelength intended or a wavelength sufficiently close to be actually used. For example, X-ray exposure devices generally use an X-ray beam having a wavelength in the range of 10 nm to 30 nm, particularly around 11 nm and 13 nm. Thus, it is desirable to evaluate their optical elements using an X-ray beam having a wavelength around that range. Subsequently, by utilizing the result from such evaluation into their manufacturing process, the optical elements are developed and manufactured quickly and efficiently. For example, one of the most important optical properties is reflectivity, and many radiation light facilities around the world have devices for evaluating reflectivity. Nevertheless, such devices are not available for any persons and can be used during limited periods of time. As such, it is difficult to evaluate optical elements for their reflectivity and implement the results quickly into their manufacturing process. Unexamined Japanese Patent Publication (Kokai) Nos. 4-128641 and 10-318945 disclose devices using a laser plasma X-ray. The contents of these publications are incorporated herein by reference in their entirety. In these devices, a laser plasma X-ray source (hereinafter referred to as an "LPX") emits an X-ray beam having a continuous spectrum, and by using a diffraction grating technique, the X-ray beam is spectrally separated. Then, by using a slit, an X-ray beam having a desired wavelength is selected. At the same time, the X-ray beam is limited a certain width with respect to that spectrum. Subsequently, the X-ray beam is irradiated upon an optical element to be measured. The reflectivity of the optical element is thus measured. However, because of the diffraction grating technique, such a method has low efficiency in using an X-ray beam. Also, because the diffraction efficiency is low, the amount of an X-ray beam reaching the optical element is low. As a result, the measurement takes longer and accuracy becomes low due to a low signal to noise ratio. In turn, it takes longer to evaluate, for example, mask blanks and X-ray optical mirrors for X-ray exposure devices during their manufacturing process, resulting in optical devices with low accuracy of measurement at a higher cost.

SUMMARY OF THE INVENTION

According to one aspect of the present invention, an optical sample X-ray testing apparatus includes an X-ray source, a line spectrum selecting device and an optical characteristics finding device. The X-ray source is configured to radiate X-rays including a group of line spectra. The line spectrum selecting device is provided between the X-ray source and an optical sample and is configured to direct substantially one line spectrum among the group of line spectra from the X-ray source toward the optical sample. The optical characteristics finding device is configured to find optical characteristics of the optical sample based on radiation of the substantially one line spectrum through the line spectrum selecting device onto the optical sample.

According to another aspect of the present invention, an optical sample X-ray testing apparatus includes an X-ray source and a line spectrum selecting device. The X-ray source is configured to radiate X-rays including a group of line spectra. The line spectrum selecting device is provided between the X-ray source and an optical sample and configured to direct substantially one line spectrum among the group of line spectra from the X-ray source toward the optical sample to find optical characteristics of the optical sample.

According to yet another aspect of the present invention, an optical sample X-ray testing apparatus includes an X-ray source, a multi-layered film mirror and an optical characteristics finding device. The X-ray source is configured to radiate X-rays including a continuous spectrum. The multi-layered film mirror is provided between the X-ray source and an optical sample and is configured to reflect only X-rays having a band range determined by the multi-layered film mirror among X-rays from the X-ray source toward the optical sample. The optical characteristics finding device is configured to find optical characteristics of the optical sample based on radiation of the X-rays having the band range determined by the multi-layered film mirror onto the optical sample.

According to further aspect of the present invention, a method for testing an optical sample with X-rays includes generating X-rays including a group of line spectra. Substantially one line spectrum among the group of line spectra is directed toward an optical sample. Optical characteristics of the optical sample are found based on radiation of the substantially one line spectrum onto the optical sample.

According to yet further aspect of the present invention, a method for testing an optical sample with X-rays includes generating X-rays including a continuous spectrum. Only X-rays having a band range determined by a multi-layered film mirror among the X-rays are reflected on the multi-layered film mirror toward an optical sample. Optical characteristics of the optical sample are found based on radiation of the X-rays having the band range determined by the multi-layered film mirror onto the optical sample.

According to the other aspect of the present invention, a method for manufacturing a reflective mask blank includes producing a mask blank configured to be exposed with X-rays. X-rays including a group of line spectra are generated. Substantially one line spectrum among the group of line spectra is directed toward the mask blank. Reflectivity of the mask blank is found based on radiation of the substantially one line spectrum onto the mask blank.

According to yet another aspect of the present invention, a method for manufacturing a mirror includes producing a mirror configured to be used in an X-ray optical system. X-rays including a group of line spectra are generated. Substantially one line spectrum among the group of line spectra is directed toward the mirror. Reflectivity of the mirror is found based on radiation of the substantially one line spectrum onto the mirror.

According to the other aspect of the present invention, a method for manufacturing a reflective mask blank includes producing a mask blank configured to be exposed with X-rays. X-rays including a continuous spectrum is generated. Only X-rays having a band width determined by a multi-layered mirror among the X-rays is reflected on the multi-layered mirror toward the mask blank. Reflectivity of the mask blank is found based on radiation of the X-rays having the band width onto the mask blank.

According to yet another aspect of the present invention, a method for manufacturing a mirror includes producing a mirror configured to be used in an X-ray optical system. X-rays including a continuous spectrum is generated. Only X-rays having a band width determined by a multi-layered mirror among the X-rays is reflected on the multi-layered mirror toward the mirror. Reflectivity of the mirror is found based on radiation of the X-rays having the band width onto the mirror.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
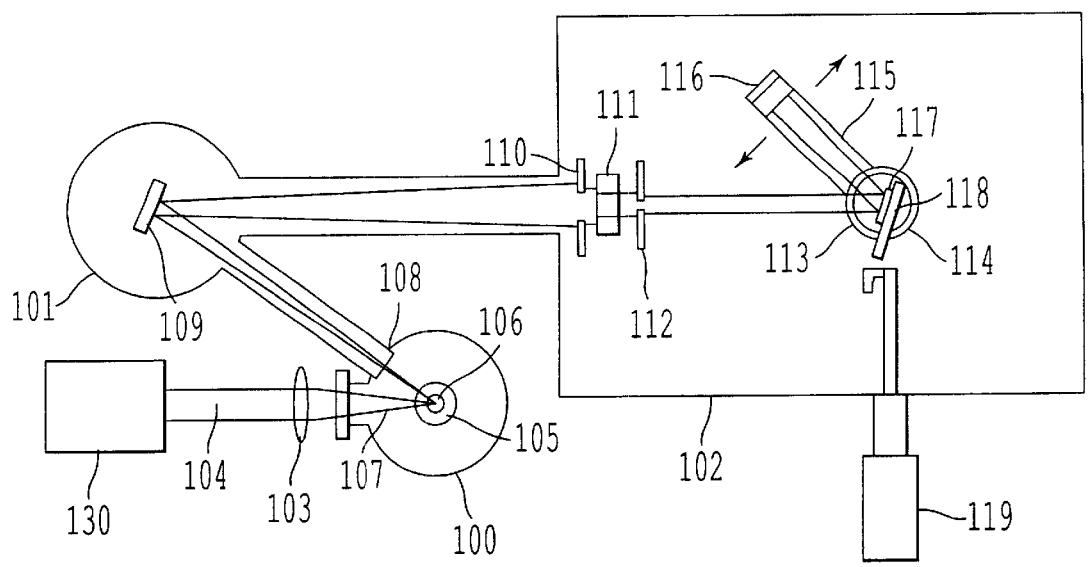
FIG. 1 is a schematic top plan view of an optical sample X-ray testing apparatus according to one embodiment of the present invention.

The preferred embodiments will now be described with reference to the accompanying drawings, wherein like reference numerals designate corresponding or identical elements throughout the various drawings.

Figure 7:
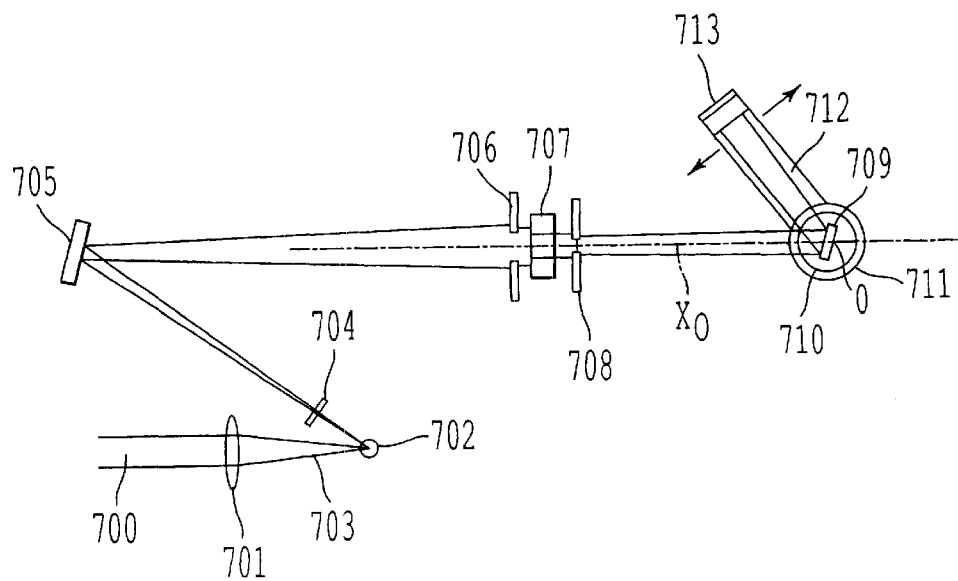
FIG. 7 is a schematic view of an optical sample X-ray testing apparatus according to one embodiment of the present invention.

FIG. 7 is a schematic view of an optical sample X-ray testing apparatus according to one embodiment of the present invention. Referring to FIG. 7, the optical sample X-ray testing apparatus finds optical characteristics of an optical sample, for example, an optical element, such as multi-layered film mirrors, oblique-incidence mirrors, filters, beam splitters. The optical characteristics are, for example, reflectivity, transmittance and degree of scattering. In FIG. 7, plasma 702 is generated by irradiating a pulse laser beam 700 upon a target material. The plasma 702 then radiates X-rays. The target material includes, for example, substances from light and middle elements or substances containing these elements. Plasma of a light element such as lithium, beryllium, boron, carbon, nitrogen, oxygen, fluorine and neon radiates dispersed line spectra. Plasma of a middle element such as sodium, magnesium, aluminum and silicon radiates more closely bundled line spectra, and there are several intense line spectra within those closely bundled line spectra. Each of these line spectra has a very narrow width, and their resolutions, $\delta\lambda/\lambda$, are approximately one few hundredth to one thousandth. Therefore, by separating one line spectrum from a group of line spectra, an X-ray beam whose monochromaticity is equal to or even better than one separated by an oblique-incident diffraction grating technique.

The X-ray emitted from the plasma 702 passes through a slit 703 and filtered by a filter 704. The slit 703 limits a portion of the filter 704 receiving particles emitted from the plasma 702 itself and its nearby. By providing such a slit, portions hidden by the slit 703 remain unused. Thus, after a certain portion has been used for a long period of time and is no longer effective as a filter because of accumulated particles, an unused portion of the filter 704 can be appropriated to filter the X-ray. Consequently, one filter lasts a long period of time. The filter 704 cuts off visible light and ultraviolet light emitted from the plasma 702, and also to prevent higher order reflection from a multi-layered film spectral separation mirror 705, the filter 704 cuts off X-rays having short wavelengths. In addition, the filter 704 separates an X-ray source side and a spectral separation mirror side. Accordingly, the X-ray source side and the spectral separation mirror side may be separately pumped by vacuuming pumps. Namely, differential pumping may be performed. The X-ray beam passed through the filter 704 is reflected by the multi-layered film spectral separation mirror 705 for spectral separation. The multi-layered film coated on the spectral separation mirror 705 is designed to reflect an X-ray beam having a predetermined wavelength and a narrow reflection band range such that among multiple line spectra radiated from the plasma, substantially one line spectrum, i.e., only one line spectrum or bundled line spectra sufficiently close to be considered as one line spectrum can be reflected off the spectral separation mirror 705.

After being separated by and reflected off the spectral separation mirror 705, the X-ray beam passes through a diaphragm 706, an Io monitor 707 for monitoring the amount of the X-ray beam incoming and a slit 708, and irradiates an optical sample 709. The diaphragm 706 adjusts the amount of the X-ray beam coming into the Io monitor 707. A pulse X-ray source such as an LPX source and a Discharge Plasma X-Ray source emit a different amount of X-ray at each pulse. Thus, it is preferably to monitor the amount of the incoming X-ray beam at each pulse by providing the Io monitor 707. The Io monitor 707 has an opening at its center such that the X-ray beam can pass through and irradiate the optical sample 709. The slit 708 adjusts a region of the optical sample 709 to be irradiated by the X-ray beam and the divergence angle of the X-ray beam.

The optical sample 709 is set upon a rotatable stage (hereinafter a "θ stage"), i.e., a first rotation mechanism 710. The θ stage is configured to rotate the optical sample 709 around a rotation axis (O) which is on the optical axis (Xo) of the X-ray beam and perpendicular to the optical axis (Xo). To measure the reflectivity of the optical sample 709, an X-ray detector (hereinafter an "Ir monitor) 713 is provided on an arm 712. The arm 712 is provided on another rotatable stage (hereinafter a "2θ stage"), a second rotation mechanism 711 which is designed to rotate around the rotation axis (O). The Ir monitor 713 is designed to measure an X-ray beam reflected off the optical sample 709. Signals from the Io monitor 707 and the Ir monitor 713 are sent to a computer which is designed to find the reflectivity of the optical sample by calculating an Ir/Io ratio. By finding the reflectivity of the optical sample 709 while the 2θ stage 711 with the Ir monitor 713 rotates for 2·δθ and the θ stage 710 with the optical sample 709 rotates for δθ, how the reflectivity of the optical sample 709 depends upon the incident angle of the X-ray beam upon the optical sample 709 can be ascertained. Based on the relationship between the reflectivity and the incident angle, the relationship between the reflectivity and the wavelength can be evaluated by calculation. For example, if the wavelength at the incident angle θ1 is λ1, then the wavelength, λ2, at the incident angle θ2 is λ1·(sin θ2/sin θ1). For more detailed conversion, it would be necessary to take the refraction index of the material forming the multi-layered film into account.

Figure 8:
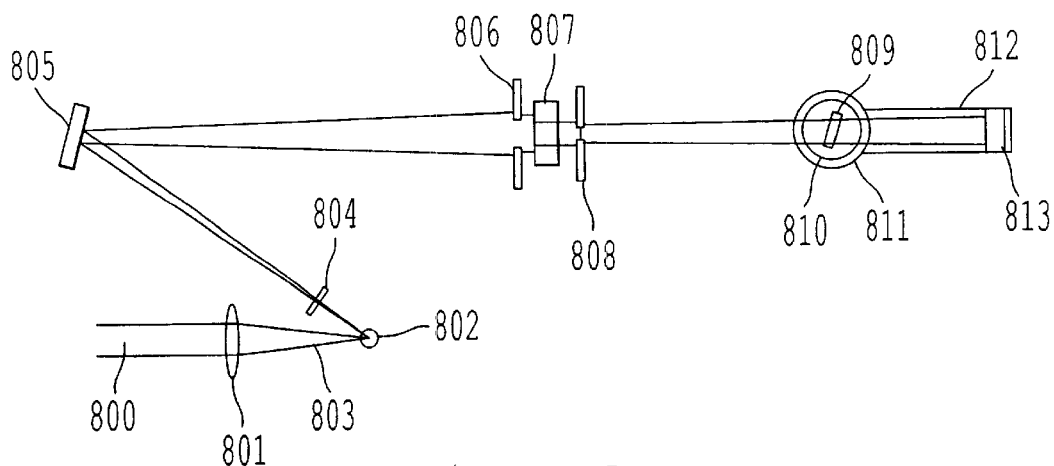
FIG. 8 is a schematic view of an optical sample X-ray testing apparatus according to one embodiment of the present invention.

FIG. 8 is a schematic view of an optical sample X-ray testing apparatus according to one embodiment of the present invention. Referring to FIG. 8, the optical sample X-ray testing apparatus according to this embodiment is designed to ascertain the transmittance of an optical sample 809. As shown in FIG. 8, for the purpose of measuring the transmittance of the optical sample 809, an (It) monitor 813 which is an X-ray detector is positioned behind the optical sample 809 with respect to the direction of an incoming X-ray beam. Signals from an (Io) monitor 808 and the It monitor 813 is sent to a computer and ascertain the transmittance of the optical sample 809 by calculating the ratio, (It/Io). At this time, the thickness of the optical sample 809 can be evaluated from its transmittance as well. For example, if the transmittance of the optical sample 809 is (T) when the X-ray beam is irradiated upon the optical sample 809 at an incident angle of θ, the thickness, (d), of the optical sample is $-\ln T \cdot (\sin \theta)/\mu$ wherein $\mu$ is the linear absorption coefficient.

When an optical sample is irradiated by a diversing X-ray beam as in this embodiment, the wavelength of its reflected X-ray beam is deviated due to the diversing of incident angle. Such a deviation should be taken into account.

Figure 9:
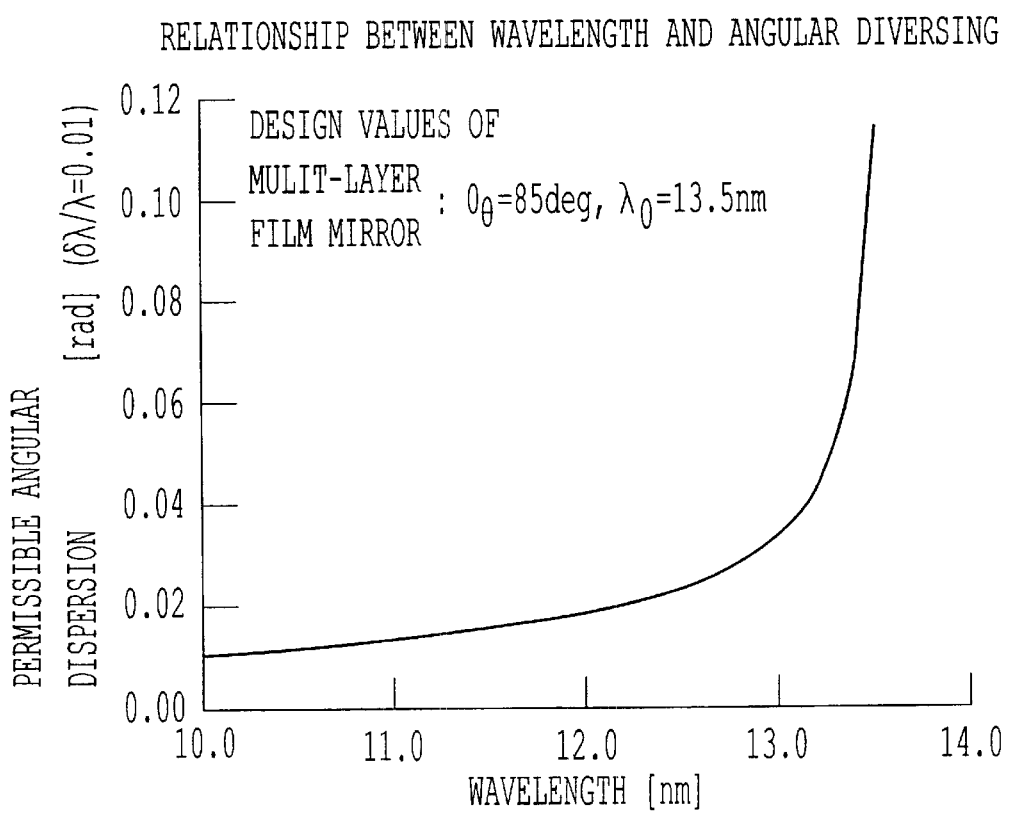
FIG. 9 is a graph of a relationship between wavelengths and the angular dispersion.

FIG. 9 is a graph of a relationship between wavelengths and the angular diversing. More specifically, the graph shows the diversing of incident angle which would permit to obtain an X-ray having a wavelength accuracy, $\delta\lambda/\lambda$, of 1%. The graph in FIG. 9 represents the result calculated for a multi-layered mirror designed to reflect off an X-ray having the wavelength of 13.5 mn when the angle of incidence is 85° as an optical sample. According to the graph, when the reflectivity is measured by using an X-ray having the wavelength of 13 nm with the wavelength accuracy, $\delta\lambda/\lambda$, of 1%, a permissible angular dispersion of the X-ray is approximately 30 mrad. With that permissible angular dispersion, a sufficient amount of the X-ray will be reflected off that multi-layered mirror for detection and measurement.

FIG. 1 is a top plan view of an optical sample X-ray testing apparatus according to one embodiment of the present invention. Referring to FIG. 1, a gas nozzle 105 is a target material discharging device and is designed to supply a target material for plasma, for example, oxygen gas, into an evacuated container 100. The gas nozzle 105 puffs the gas in a direction perpendicular to the drawing paper of FIG. 1 from back surface to the front surface of the paper. The evacuated container 100 is evacuated, for example, by a vacuuming device to a pressure level where a laser beam would not discharge and an X-ray radiated by a plasma would not get weakened by absorption. Vacuum containers 101, 102 are also depressurized such that an X-ray radiated by a plasma would not get weakened by absorption. A laser device 130 emits a pulse laser beam 104 and a lens 103 converges the pulse laser beam to a point which is about 0.5 mm above the gas jet nozzle 105. Thus, a plasma 106 can be generated. The plasma 106 has the shape of a filament extending toward the source of the pulse laser beam in a length of approximately 300 μm and a width of approximately 100 μm.

Figure 2A:
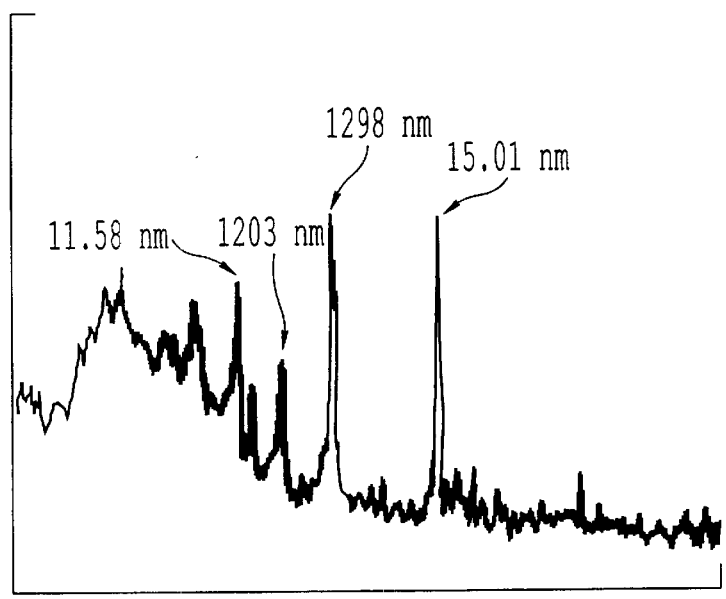
FIG. 2(a) is a graph of a spectrum obtained from a Laser Plasma X-ray source using oxygen gas as a target.
Figure 2B:
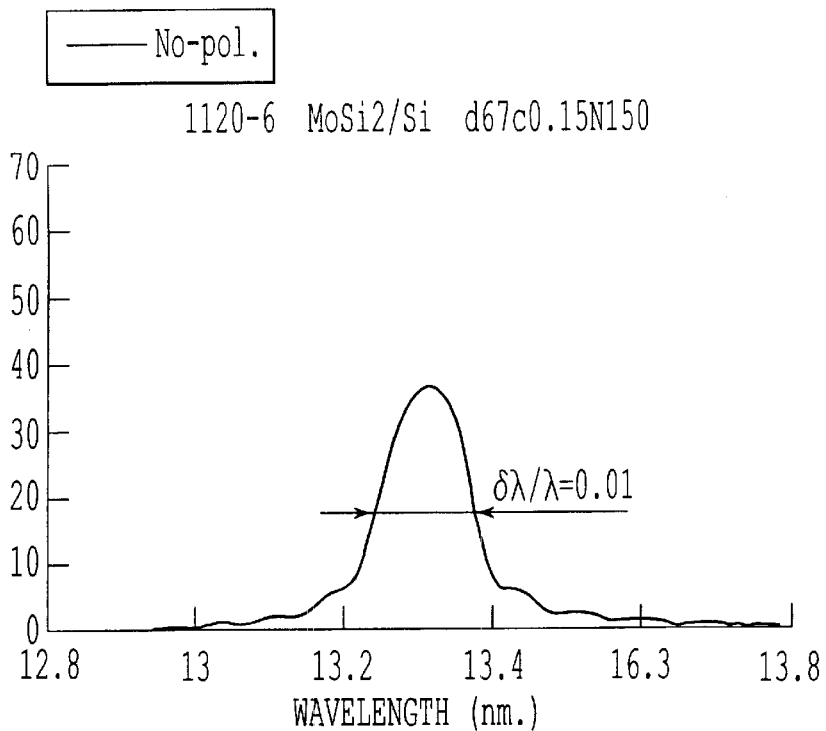
FIG. 2(b) is a graph of reflection spectrum of a $MoSi_2/Si$ multi-layered film mirror for spectral diffraction.

FIG. 2(*a*) is a graph of an exemplary spectrum obtained from a Laser Plasma X-ray source using oxygen gas as a target. Referring to FIG. 2(*a*), the exemplary spectrum shows that the plasma is irradiating several line spectra which are characteristics of oxygen. Among those line spectra, line spectra of 12.98 nm and 15.01 nm from $O^{5+}$ ion are intensely radiated and are close to the wavelength of 13 nm suitable for an X-ray reduction exposure device. The widths of the line spectra in FIG. 2(*a*) are dependent upon the resolution of the spectrometer used in this experiment and thus much wider than the actual widths of the line spectra.

An X-ray emitted from the plasma 106 passes though a slit 107, is filtered by a Be filter 108 having a thickness of 1 μm, and is reflected by a multi-layered film flat mirror 109 for spectral separation. The Be filter cuts off the visible light, the UV light and the lights whose wavelengths are below 11 nm. The X-ray is irradiated upon the multi-layered film flat mirror 109 at the grazing incident angle of 75°.

The multi-layered film flat mirror 109 utilizes a multi-layered film made from $MoSi_2$ and Si. FIG. 2(*b*) shows a reflection spectrum which is predicted based on calculation of a multi-layered film including 150 pairs of $MoSi_2$ and Si layers, for example. This multi-layered film is designed such that the range of bands for reflection is narrowed as much as possible. As seen from FIG. 2(*b*), the range of bands for reflection is narrowed down to approximately 1%. By using $MoSi_2$/Si for a multi-layered film as such, the range of bands for reflection can be narrowed and thus only one desired line spectrum can be reflected off the multi-layered film flat mirror 109. In this embodiment, the multi-layered film flat mirror 109 uses a $MoSi_2$/Si multi-layered film whose periodic length is designed such that the wavelength at the center is 12.98 nm. As a result, in the spectrum shown in FIG. 2(*b*), only the line spectrum of 12.98 nm is reflected. More accurately, the line spectrum of 12.98 nm is made up from two extremely close line spectra, the line spectra of 12.9871 nm and 12.9758 nm. However, because ranges of bands for reflection in X-ray optical elements actually in use are much broader than the wavelength difference between these two line spectra, these two line spectra can be considered as one line spectra for the purpose of evaluating an optical element.

Referring to FIG. 1, after being reflected from the multi-layered film flat mirror 109, the X-ray beam passes through a diaphragm 110 and an Io monitor 111 equipped with a micro-channel plate (hereinafter "MCP") having an opening. Subsequently, the X-ray passes through a slit 112 and irradiates an optical sample 117. The diaphragm 110 is provided to adjust the amount of the X-ray beam entering into the Io monitor 111, and the slit 112 is provided to limit a region of the optical sample 117 to be irradiated by the X-ray beam as well as the X-ray beam's angle of divergence. Since the optical axis of the X-ray beam passing through the Io monitor 111 and the optical axis of the X-ray beam irradiating the optical sample 117 are extremely close by, the X-ray beam of a certain line spectrum passes through the Io monitor 111 and irradiate the optical sample at substantially the same intensity. In other words, there is a correlation between an intensity detected by the Io monitor 111 and an intensity of the X-ray beam irradiating the optical sample 117.

The optical sample 117 is positioned upon a rotatable stage (hereinafter a "θ stage") 113 and can be rotated with respect to the direction from which the X-ray beam is irradiating. Also, the optical sample 117 is held by a holder 118 which can be set in and removed from the θ stage 113 by a setting device 119. Furthermore, a secondary rotatable stage (hereinafter a "2θ stage") 114 is provided. The 2θ stage 114 can rotate around the same axis of rotation as the θ stage 113 and is attached to an arm 115. The arm 115 is attached to an MCP (hereinafter an "Ir monitor") 116 which measures an X-ray beam reflected from the optical sample 117. Signals from the Io monitor 111 and the Ir monitor 116 pass through a field-through and are received by a digital oscilloscope.

Reflectivity is measured as follows. First, the setting device 119 moves the optical sample 117 to a position where the optical sample does not get irradiated by the incoming X-ray beam. The 2θ stage 114 rotates and positions the Ir monitor 116 to receive the X-ray beam. Under this setting, the X-ray is generated and the signals from the Io monitor 111 and the Ir monitor 116 are sent to the digital oscilloscope. Preferably, several signals or even tens of signals are averaged at this time for the purposes of reducing random noise and increasing the signal to noise ratio. A waveform thus input into the digital oscilloscope is a time waveform of the X-ray beam radiated from the plasma. The waveform in the digital oscilloscope is transferred into a computer, for example, through a GPIB. Then, the output signal voltages from the Io monitor 111 and the Ir monitor 116 are divided by an input impedance (for example, 50 Ω) of the digital oscilloscope and the values thus obtained are integrated for time. The values from the integrations are the amounts (Qo and Qro) of the charges sent from the Io monitor 111 and the Ir monitor 116. These charges, (Qo and Qro), are proportional to the amounts of the X-ray beam irradiated upon the Io monitor 111 and the Ir monitor 116, respectively. The ratio Qro/Qo obtained under this setting becomes a calibration value (C). To accurately obtain the calibration value (C), preferably, the process just mentioned above is repeated several times and an average value is used as the calibration value (C). Once the calibration value (C) is determined, the setting device 119 moves the optical sample 117 to a position where the X-ray beam can irradiate the optical sample 117. Then, the Io monitor 111 and the Ir monitor 116 take measurements as the 2θ stage 114 makes a (2·δθ) rotation while the θ stage 113 makes a (δθ) rotation. Signals at a ceratin angle (θ), Io and Ir(θ), are integrated in the same manner previously described. After finding out the amount of charges Qo and Qr(θ), their ratio, Qr(θ)/Qo, can be calculated. Then, by multiplying the calibration value (C) determined beforehand to the ratio, Qr(θ)/Qo, reflectivity at the certain angle (θ) can be ascertained. In other words, reflectivity can be ascertained from the equation, R(θ)=C·(Qr(θ)/Qo). By repeating the procedure described above for various angles in a certain range, reflectivities over that range of angles for the optical sample 117 can be obtained.

Figure 3:
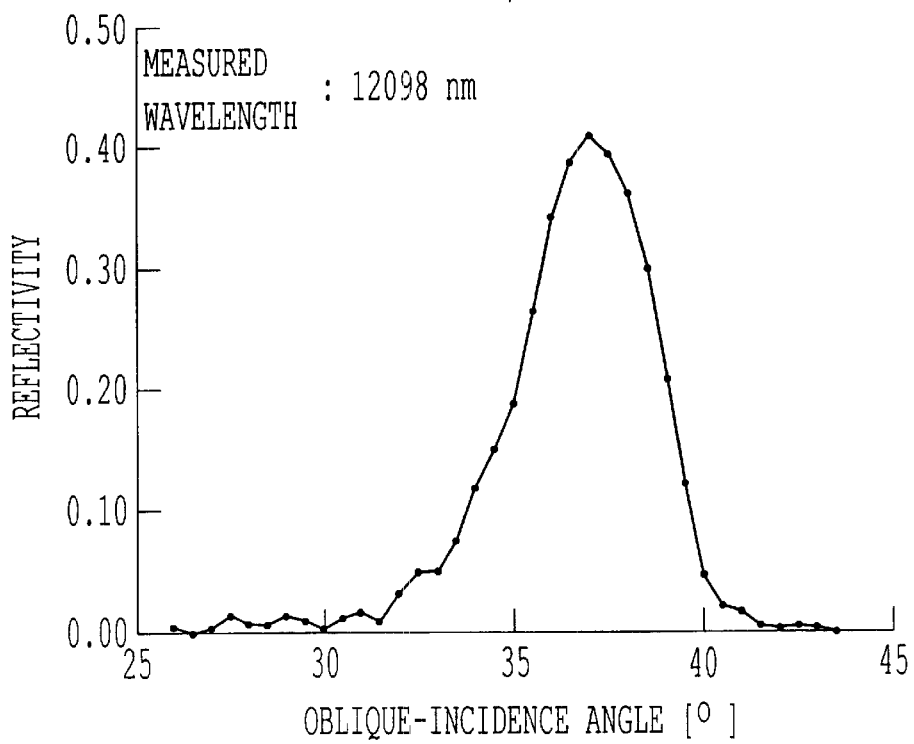
FIG. 3 is a graph of an experimental result for a reflective property of a multi-layered film mirror as measured by the optical sample X-ray testing apparatus shown in FIG. 1.

FIG. 3 shows a graph displaying reflectivities over a certain range of angles obtained for a multi-layered film mirror by using the method described above. In this measurement, the optical sample, i.e., the multi-layered film mirror, was a Mo/Si multi-layered film mirror. Also, in this measurement, the waveform from the Io monitor 111 and the Ir monitor 116 were integrated by the computer. Nonetheless, the signals from the Io monitor 111 and the Ir monitor 116 can be integrated by a hardware using an integration circuit, and the peak values of their respective signals thus output can be input into the computer. By doing so, load on the computer can be reduced and thus a more high repetition rate LPX can be handled. Still, if the time waveform of the X-ray is stable, instead of performing the integration, the reflectivity, (Irpeak)/(Iopeak), can be calculated from the respective peak values of the Io waveform and the Ir waveform. Further, in this experiment, oxygen was used as a target material for the LPX. However, any substances containing oxygen can be used for this purpose. Also, instead of gas, the target material can be in any states such as liquid, solid, a cluster, particles, a mixture of particles and a liquid, a mixture of a gas and particles. For example, water, steam, carbon dioxide, sulfuric acid can be used for the target material. Especially, unlike oxygen, carbon dioxide does not explode or ignite, and it is inexpensive. Moreover, because carbon dioxide contains carbon which does not radiate intense line spectra around 13 nm, it does not interfere with the measurement. Sulfuric acid has a low vapor pressure and does not raise the pressure within the target chamber. Thus, it is a stable target material to use for this purpose. For instance, at 20° C., an 80% solution of sulfuric acid has a vapor pressure of 0.0835 mmHg which is sufficiently lower than the pressure usually produced in the target chamber for LPX. Also, because hydrogen and sulfur contained in sulfric acid do not radiate intense line spectra around 13 nm, they do not interfere with the measurement. These target materials can be supplied in various methods such as a form of a tape and drops as well as the gas jet employed in this embodiment.

In this embodiment, because of the oxygen ion capable of radiating the X-ray beam having the wavelength of 12.98 nm, oxygen is used for the target material. Nevertheless, any substances can be used for the target material as long as they can radiate a X-ray beam having a wavelength close to the wavelength used in an optical element to be examined. For example, lithium can be used to radiate a line spectrum of 13.5 nm, fluorine to radiate line spectra of 13.5 nm and around 14 nm, neon to radiate intense line spectra of 10.3 nm, 10.6 nm and 11.1 nm, sodium to radiate an intense line spectrum of around 12.5 nm, magnesium to radiate intense line spectra of 11.5 nm, 13.2 nm and 13.7 nm, aluminum to radiate intense line spectra of 10.4 nm, 11.0 nm and 13.1 nm, and silicon to radiate intense line spectra of 11.8 nm and 11.9 nm. When lithium is used for the target material, it is preferable to use it in a form of lithium hydride (LiH) or lithium hydroxide (LiOH) since lithium itself is very unstable. Similarly, because sodium itself is extremely unstable, sodium chloride (NaCl) or sodium hydroxide (NaOH) should be used. For fluorine, because fluorine gas itself is extremely reactive, a solid form such as TEFLON or a gaseous form such as carbon tetrafluoride ($CF_4$) or sulfur hexafluoride ($SF_6$) should be used as the target material. In these situations, the target material can be in any states such as gas, liquid, solid, a cluster and particles.

Furthermore, in this embodiment, MCPs are used for the Io monitor 111 and the Ir monitor 116. However, any detectors can be used in its place as long as they can detect an X-ray beam used in the measurement. For example, semiconductor elements such as a photo diode for X-ray, CCD and a linear photo diode array can be used for the Io monitor 111 and the Ir monitor 116. Unlike an MCP, these semiconductor elements do not require high vacuum, i.e., about less than $10^{-6}$ (Torr), and thus cut the time required to evacuate the apparatus. As a result, the operation of the apparatus becomes more efficient. Also, the use of these semiconductor elements increase the versatility in designing the apparatus and cut down the cost for mass production.

A slit can be placed immediately in front of the Ir monitor 116 in order to cut off any scattered beam from the optical sample 117. On the other hand, in order to find out how much scattering is occurring, the slit in front of the Ir monitor 116 can be narrowed and the Ir monitor 116 is rotated to measure the intensity distribution of the reflected beam while the optical sample 117 is held in its position. As such, the scattering of the beam can be observed. Still, instead of the slit, by placing a knife edge immediately in front of the Ir monitor 116, the intensity of the reflected X-ray beam can be measured while the knife edge is being scanned. Therefore, the degree of the scattering can be measured.

Finally, in this embodiment, the optical sample 117 and the detector for the reflected X-ray beam, i.e., the Ir monitor 116, are designed to be rotated. However, if the measurement is to be taken at a certain predetermined or known angle, the optical sample 117 and the detector 116 can be affixed in place. For example, to determine simply whether the optical sample is good or bad, such a method would increase the efficiency of the determination.

Figure 4:
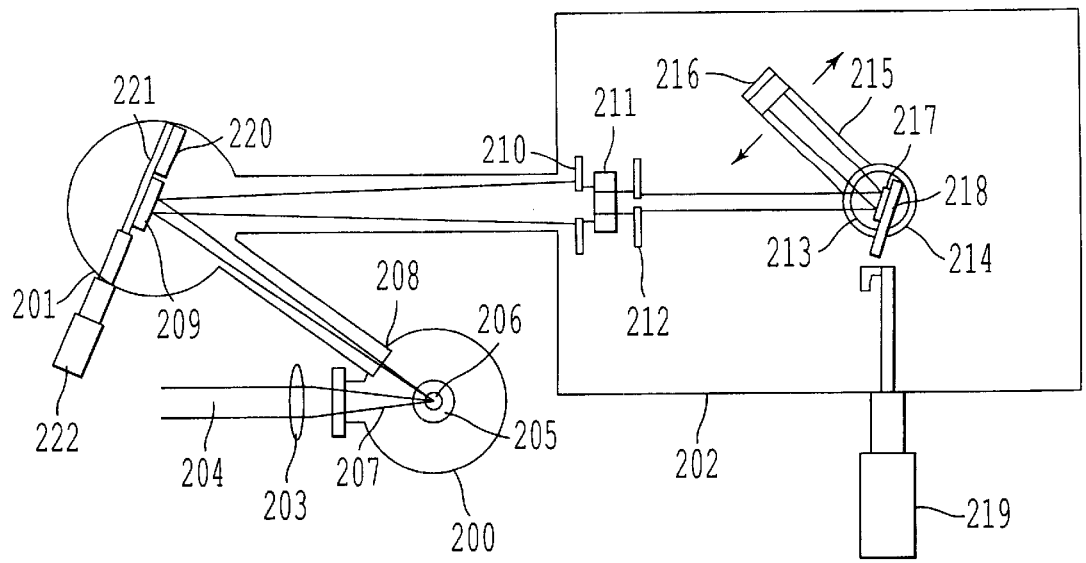
FIG. 4 is a schematic view of an optical sample X-ray testing apparatus according to another embodiment of the present invention.

FIG. 4 is a top plan view of an optical sample X-ray testing apparatus according to another embodiment of the present invention. Referring to FIG. 4, the optical sample X-ray testing apparatus according to this embodiment is equipped with a plurality of multiple-layered film mirrors, for example, two multiple-layered film mirrors 209, 220 for spectral separation. By providing more than one multiple-layered film mirror, the optical sample X-ray testing apparatus permits the selection of a multiple-layered film mirror designed to reflect an X-ray beam having a desired wavelength easily.

Each of these two multiple-layered film mirrors 209, 220 uses a $MoSi_2$/Si multiple-layered film; however, these two multiple-layered film mirrors 209, 220 have different periodic lengths. In this embodiment, the two multiple-layered film mirrors 209, 220 are designed to separate the line spectra of oxygen ion, one multiple-layered film mirror 209 having a reflection wavelength of, for example, 12.98 nm and the other multiple-layered film mirror 220 having a reflection wavelength of, for example, 15.01 nm. A mirror setting device 222 is designed to switch these two multiple-layered film mirrors 209, 220 in vacuum and position one of them for measurement. Hence, the measurements of reflectivities can be carried out with X-ray beams having two different wavelengths without disturbing the vacuum. Additionally, by providing multiple target materials for LPX and a number of spectral separation mirrors having different reflection wavelengths respective of the line spectra to be radiated from the target materials, the measurements of reflectivities can be carried out with X-ray beams having broader wavelengths region.

Figure 5:
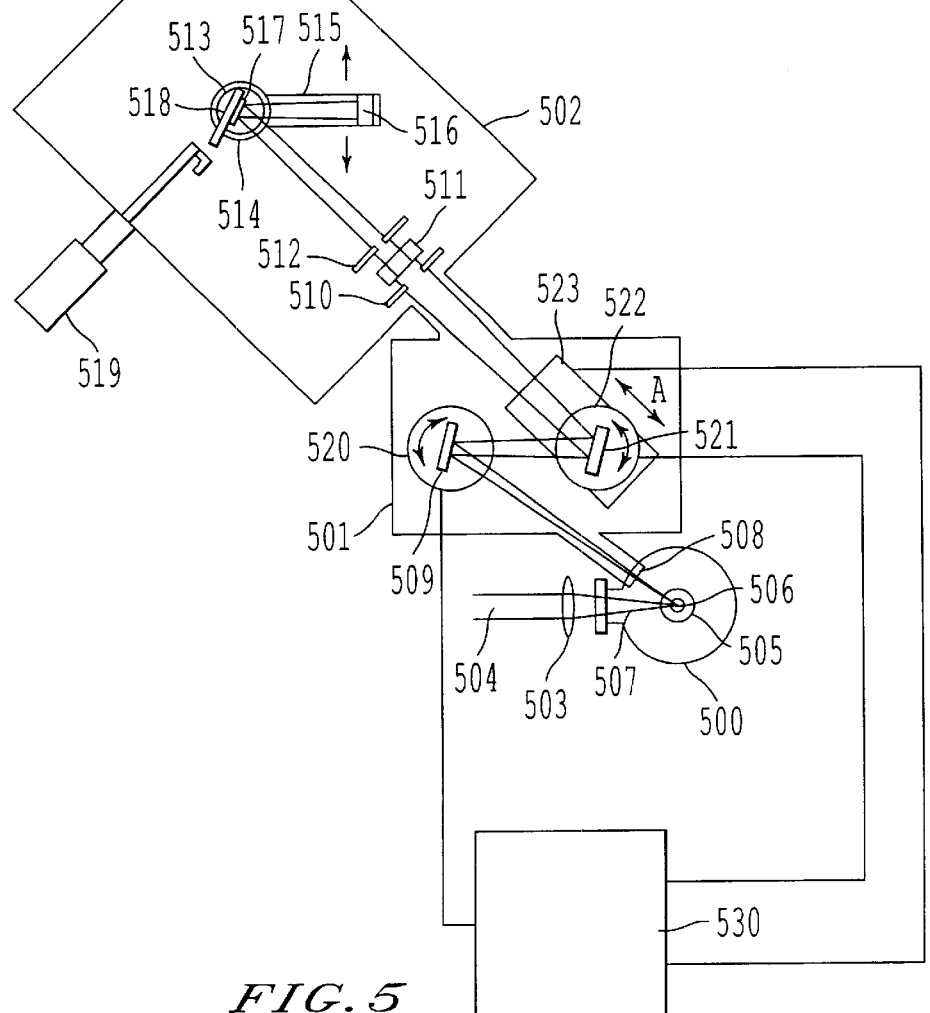
FIG. 5 is a schematic view of an optical sample X-ray testing apparatus according to yet another embodiment of the present invention.

FIG. 5 is a top plan view of an optical sample X-ray testing apparatus according to yet another embodiment of the present invention. Referring to FIG. 5, the optical sample X-ray testing apparatus of this embodiment is equipped with a first multiple-layered film mirror 509 for first spectral separation and a second multiple-layered film mirror 521 for second spectral separation. The first multiple-layered film mirror 509 is provided on a first rotatable stage 520 such that the first multiple-layered film mirror 509 can be rotated in the direction of the incoming X-ray beam. Likewise, the second multiple-layered film mirror 521 is provided on a second rotatable stage 522 such that the second multiple-layered film mirror 521 can be rotated in the direction of the incoming X-ray beam. The second rotatable stage 522 is provided on a movable stage 523 such that the second rotatable stage 522 can be moved linearly in the direction (A) as shown in FIG. 5. Both the first and second multiple-layered film mirrors 509, 521 use a $MoSi_2$/Si multiple-layered film having the same periodic length. In this embodiment, by changing the angle of the first multiple-layered film mirror 509, i.e., rotating the first multiple-layered film mirror 509, the wavelength of the X-ray being reflected changes. Furthermore, by using the second rotatable stage 522 and the movable stage 523, the angle and position of the second multiple-layered film mirror 521 can be adjusted to compensate the change in the angle of the first multiple-layered film mirror 509. As a result, the X-ray beam is reflected off the second multiple-layered film mirror 521 always to a substantially constant direction. A controller 530 is configured to control a rotation of the first multiple-layered film mirror 509 and rotational and linear movements of the second multiple-layered film mirror 521 to reflect the substantially one line spectrum from the first multi-layered film mirror 509 to the substantially constant direction. By utilizing these two multiple-layered film mirrors 509, 521 as such, the wavelength of the X-ray beam to be radiated upon the optical sample 517 can be altered without changing the optical axis of the X-ray beam and without replacing the mirror for spectral separation. For example, in an optical sample X-ray testing apparatus using oxygen for the target material, reflectivity measurement over a range of angles can be carried out with the line spectrum of 12.98 nm followed by reflectivity measurement with the line spectrum of 15.01 nm by changing the angles of the first and second multiple-layered film mirrors 509, 521. In addition, because the X-ray beam is reflected twice, the band width of reflection becomes narrower and thus the monochromaticity of the X-ray beam increases.

In this embodiment, both the first and second multi-layered film mirrors 509, 520 are flat mirrors. However, these first and second multi-layered film mirrors 509, 520 can be in any forms. For example, the first multi-layered film mirror 509 may be a flat mirror while the second multi-layered film mirror 520 may be a spherical mirror.

Figure 6:
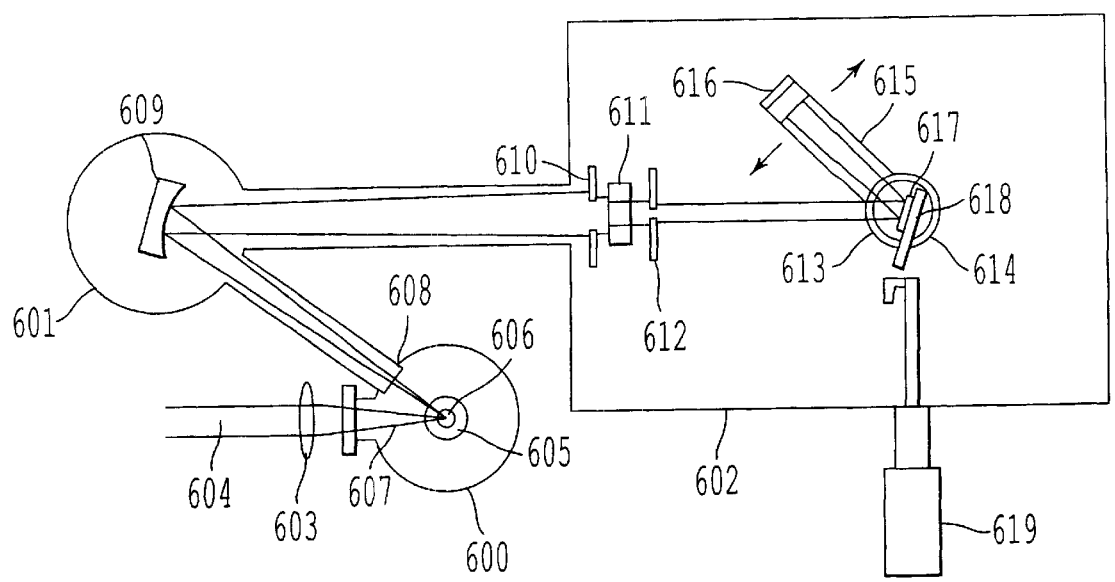
FIG. 6 is a schematic view of an optical sample X-ray testing apparatus according to still another embodiment of the present invention.

FIG. 6 is a top plan view of an optical sample X-ray testing apparatus according to still another embodiment of the present invention. Referring to FIG. 6, the optical sample X-ray testing apparatus of this embodiment is equipped with an elliptical spectral separation mirror 609. The elliptical spectral separation mirror 609 is positioned such that one of the two foci is at a plasma 606 while the other one is at an optical sample 617. Further, the elliptical spectral separation mirror 609 is coated with a $MoSi_2/Si$ multi-layered film. Preferably, the periodic length of the $MoSi_2/Si$ multi-layered film changes depending on the incident angle of the X-ray beam coming into the elliptical spectral separation mirror 609 in order to obtain a high reflectivity. Compared to a flat mirror, an elliptical mirror permits a larger solid angle for the incoming X-ray beam. Thus, the optical sample 617 is irradiated with a larger amount of the X-ray beam, resulting in a higher signal to noise ratio, S/N, to permit higher accuracy for measurement. Also, because the X-ray beam irradiates a much smaller region of the optical sample 617, the dimensional distribution of the reflectivities over the surface of the optical sample 617 can be observed by scanning positions on the optical sample 617.

In this embodiment, the elliptical spectral separation mirror 617 is used. However, a spherical surface mirror or a parabolic surface mirror may be used in its place. Compared to an elliptical mirror, a spherical surface mirror falls behind in the ability to condense light; however, a spherical surface mirror is less expensive to obtain because it is easier to process its substrate. A parabolic surface mirror reflects an-X-ray beam in the form of a parallel beam, and thus the need for considering the diversing angle of the X-ray beam radiating an optical sample is eliminated.

Although, in each of the embodiments described thus far, a $MoSi_2/Si$ multi-layered film is employed for spectral separation, any multi-layered films can be used as long as they possess a sufficiently narrow band range and sufficient reflectivity for an X-ray beam to be used.

Furthermore, in each of the embodiments described thus far, an LPX is used for the source of X-ray beams. Nevertheless, any X-ray sources, for example, Dense Plasma Focus, Z Pinch Plasma and Discharge Plasma X-Ray Source using capillary, may be used.

Also, in each of the embodiments described thus far, an X-ray source which radiates line spectra is used. However, an X-ray source which radiates a continuous spectrum may be used. By using substances having a large atomic number such as tungsten, tantalum, gold, tin, krypton and xenon as the target material, an LPX and a Discharge Plasma X-Ray source emit a continuous spectrum. For an X-ray beam having a continuous spectrum, the width of the spectrum can be monochromatic only to the extent of the band width of a multi-layered film mirror. Nonetheless, reflectivity and angle distribution can be roughly ascertained. Also, by using an X-ray beam having a continuous spectrum in the apparatus shown in FIG. 5, the wavelength of the X-ray may be continuously changed. Thus, not only a range of angles but also a range of wavelengths may be scanned. In addition, an X-ray beam having a continuous spectrum permits use of an entire X-ray beam within the reflection band range of a separation mirror. Accordingly, an X-ray beam having a continuous spectrum radiates more upon an optical sample than an X-ray beam having line spectra. As a result, the time of measurement can be reduced by using an X-ray beam having a continuous spectrum.

According to the above described embodiments, an LPX or Discharge Plasma X-Ray source which has a small size is used. Accordingly, the entire size of the optical sample X-ray testing apparatus may reduce. The optical sample X-ray testing apparatus may be set at manufacturing locations of optical elements. Therefore, optical elements can be evaluated easily and the result of the evaluation can be implemented quickly into their processing and manufacturing methods. Furthermore, in the embodiments, monochromatic X-rays are obtained by selecting substantially one line spectrum from the group of line spectra radiated from the X-ray source using the multi-layered film mirror. Therefore, an efficiency in using X-rays and accuracy for measurement may increase. Further, in the embodiments, a diffraction grating is not used. Accordingly, testing the characteristics of the optical sample may be easier because accurate positioning is not necessary.

By using a substance containing oxygen, fluorine, neon or lithium as the target material for the LPX or the Discharge Plasma X-Ray source, an X-ray beam having line spectra in the range of 10 nm to 14 nm. Such an X-ray beam is suitable for X-ray reduction exposure devices and thus also suitable for evaluating optical elements for the X-ray reduction exposure devices.

Figure 10:
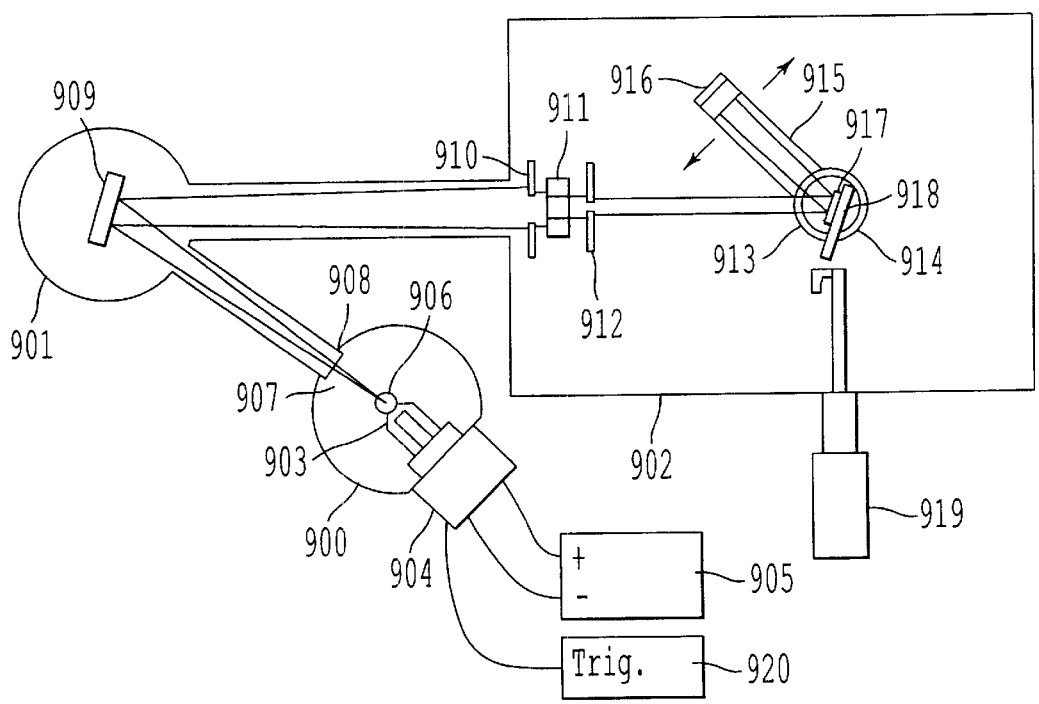
FIG. 10 is a schematic view of an optical sample X-ray testing apparatus according to one embodiment of the present invention.

FIG. 10 is a top plan view of an optical sample X-ray testing apparatus according to still another embodiment of the present invention. Referring to FIG. 10, a discharge plasma X-ray source includes a charging and switching device 904 which is connected to a high voltage electric source 905 and a trigger device 920. The trigger device 920 triggers the charging and switching device 904. Accordingly, a DPF electrode 903 discharges electricity toward a target material to generate plasma thereby radiating X-rays.

A mask blank which is configured to be exposed with X-rays is produced. Then, the mask blank is tested whether the reflectivity of the mask blank is higher than a predetermined reference value. As shown in FIG. 1, X-rays including a group of line spectra is generated. Then substantially one line spectrum among the group of line spectra is reflected toward the mask blank. The reflectivity of the mask blank is found based on radiation of the substantially one line spectrum onto the mask blank.

A mirror which is configured to be used in an X-ray optical system is produced. Then, the mirror is tested whether the reflectivity of the mirror is higher than a predetermined reference value. As shown in FIG. 1, X-rays including a group of line spectra is generated. Then substantially one line spectrum among the group of line spectra is reflected toward the mirror. The reflectivity of the mirror is found based on radiation of the substantially one line spectrum onto the mirror.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An optical sample X-ray testing apparatus, comprising:
    an X-ray source configured to radiate X-rays including a group of spectra;
    a filter provided between the X-ray source and an optical sample and configured to cut off visible light and UV light;
    at least one line spectrum selecting device provided between the X-ray source and the optical sample and configured to direct substantially one line spectrum among the group of line spectra from the X-ray source toward the optical sample; and
    an optical characteristics finding device configured to find optical characteristics of the optical sample based on radiation of the substantially one line spectrum through the line spectrum selecting device onto the optical sample, wherein the line spectrum selecting device comprises at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra.

2. An optical sample X-ray testing apparatus according to claim 1, wherein the X-ray source comprises:
   a container which is configured to be evacuated and to which a target material is configured to be supplied; and
   a laser source configured to radiate laser beam to the target material to generate plasma.

3. An optical sample X-ray testing apparatus according to claim 2, wherein the target material comprises either oxygen (O), fluorine (F), neon (Ne), lithium (Li), sodium (Na), magnesium (Mg) or aluminum (Al).

4. An optical sample X-ray testing apparatus according to claim 2, wherein the target material comprises a material which is configured to radiate X-rays whose wave length is substantially same as that of X-rays which are practically used for the optical sample.

5. An optical sample X-ray testing apparatus according to claim 1, wherein the X-ray source comprises a discharge plasma X-ray source.

6. An optical sample X-ray testing apparatus according to claim 1, wherein the multi-layered film mirror comprises a plurality of layers which is made of a material which has narrow band range and high reflectivity with respect to X-rays.

7. An optical sample X-ray testing apparatus according to claim 1, wherein the multi-layered film mirror comprises a plurality of $MoSi_2$/Si layers.

8. An optical sample X-ray testing apparatus according to claim 1, wherein the line spectrum selecting device comprises:
   a plurality of multi-layered film mirrors which have different periodic length; and
   a selector configured to select one of the plurality of multi-layered film mirrors to reflect the substantially one line spectrum among the group of line spectra.

9. An optical sample X-ray testing apparatus according to claim 1, wherein the line spectrum selecting device comprises:
   a first multi-layered film mirror configured to rotate around a first axis and to reflect the substantially one line spectrum among the group of line spectra from the X-ray source;
   a second multi-layered film mirror configured to rotate around a second axis, move linearly and reflect the substantially one line spectrum from the first multi-layered film mirror, the second multi-layered film mirror having a periodic length same as that of the first multi-layered film mirror; and
   a controller configured to control a rotation of the first multi-layered film mirror and rotational and linear movements of the second multi-layered film mirror to reflect the substantially one line spectrum from the first multi-layered film mirror toward a constant direction.

10. An optical sample X-ray testing apparatus according to claim 9, wherein the first and second multi-layered film mirrors are flat mirrors.

11. An optical sample X-ray testing apparatus according to claim 9, wherein the first multi-layered film mirror is a flat mirror and wherein the second multi-layered film mirror is a spherical mirror.

12. An optical sample X-ray testing apparatus according to claim 2, wherein the line spectrum selecting device comprises a multi-layered film mirror which is configured to reflect the substantially one line spectrum among the group of line spectra, the multi-layered film mirror having an elliptical reflective surface and being positioned such that one of two foci of the elliptical reflective surface is located at the plasma and another of the two foci of the elliptical reflective surface is located at the optical sample.

13. An optical sample X-ray testing apparatus according to claim 1, wherein the multi-layered film mirror is a flat mirror, a spherical mirror, an elliptical mirror, or a paraboloid mirror.

14. An optical sample X-ray testing apparatus according to claim 1, wherein the optical characteristics finding device is configured to find reflectivity, transmittance or scattering degree of the optical sample.

15. An optical sample X-ray testing apparatus, comprising:
   an X-ray source configured to radiate X-rays including a group of line spectra;
   at least one line spectrum selecting device provided between the X-ray source and an optical sample and configured to direct substantially one line spectrum among the group of line spectra from the X-ray source toward the optical sample; and
   an optical characteristics finding device configured to find optical characteristics of the optical sample based on radiation of the substantially one line spectrum through the line spectrum selecting device onto the optical sample,
   wherein the line spectrum selecting device comprises at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra, and
   wherein the optical characteristics finding device comprises:
      an incidence amount detector configured to detect an amount of X-rays which are radiated to the optical sample; and
      a reflection amount detector configured to detect an amount of X-rays which are reflected from the optical sample.

16. An optical sample X-ray testing apparatus according to claim 15, further comprising:
   a first rotation mechanism configured to rotate the optical sample around a rotation axis which is on an optical axis of the X-rays which are radiated to the optical sample and which is perpendicular to the optical axis; and
   a second rotation mechanism configured to rotate the reflection amount detector around the rotation axis to receive the X-rays reflected by the optical sample.

17. An optical sample X-ray testing apparatus, comprising:
   an X-ray source configured to radiate X-rays including a group of line spectra;
   at least one line spectrum selecting device provided between the X-ray source and an optical sample and configured to direct substantially one line spectrum among the group of line spectra from the X-ray source toward the optical sample; and an optical characteristics finding device configured to find optical characteristics of the optical sample based on radiation of the substantially one line spectrum through the line spectrum selecting device onto the optical sample, wherein the line spectrum selecting device comprises at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra, and wherein the optical characteristics finding device comprises:
an incidence amount detector configured to detect an amount of X-rays which are radiated to the optical sample; and
a transmission amount detector configured to detect an amount of X-rays which the optical sample transmits.

18. An optical sample X-ray testing apparatus, comprising:
an X-ray source configured to radiate X-rays including a group of line spectra;
a filter provided between the X-ray source and an optical sample and configured to cut off visible light and UV light; and
at least one line spectrum selecting device provided between the X-ray source and the optical sample and configured to direct substantially one line spectrum among the group of line spectra from the X-ray source toward the optical sample to find optical characteristics of the optical sample,
wherein the line spectrum selecting device comprises at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra.

19. An optical sample X-ray testing apparatus, comprising:
X-ray source means for radiating X-rays including a group of line spectra;
filter means for cutting off visible light and UV light, the filter means being provided between the X-ray source and an optical sample;
line spectrum selecting means for directing substantially one line spectrum among the group of line spectra from the X-ray source toward the optical sample, the line spectrum selecting means being provided between the X-ray source means and the optical sample; and
an optical characteristics finding means for finding optical characteristics of the optical sample based on radiation of the substantially one line spectrum through the line spectrum selecting means onto the optical sample,
wherein the line spectrum selecting means comprises at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra.

20. An optical sample X-ray testing apparatus, comprising:
an X-ray source configured to radiate X-rays including a continuous spectrum;
a filter provided between the X-ray source and an optical sample and configured to cut off visible light and UV light;
at least one multi-layered film mirror provided between the X-ray source and the optical sample and configured to reflect only X-rays having a band width determined by the multi-layered film mirror among X-rays from the X-ray source toward the optical sample; and
an optical characteristics finding device configured to find optical characteristics of the optical sample based on radiation of the X-rays having the band range determined by the multi-layered film mirror onto the optical sample.

21. A method for testing an optical sample with X-rays, comprising:
generating X-rays including a group of line spectra;
cutting off visible light and UV light by using a filter;
directing substantially one line spectrum among the group of line spectra toward an optical sample by using at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra; and
finding optical characteristics of the optical sample based on radiation of the substantially one line spectrum onto the optical sample.

22. A method for testing an optical sample with X-rays, comprising:
generating X-rays including a continuous spectrum;
cutting off visible light and UV light by using a filter;
reflecting on at least one multi-layered film mirror only X-rays having a band range determined by the multi-layered film mirror among the X-rays toward an optical sample; and
finding optical characteristics of the optical sample based on radiation of the X-rays having the band range determined by the multi-layered film mirror onto the optical sample.

23. A method for manufacturing a reflective mask blank, comprising:
producing a mask blank configured to be exposed with X-rays;
generating X-rays including a group of line spectra;
cutting off visible light and UV light by using a filter;
directing substantially one line spectrum among the group of line spectra toward the mask blank by using at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra; and
finding reflectivity of the mask blank based on radiation of the substantially one line spectrum onto the mask blank.

24. A method for manufacturing a mirror, comprising:
producing a mirror configured to be used in an X-ray optical system;
generating X-rays including a group of line spectra;
cutting off visible light and UV light by using a filter;

directing substantially one line spectrum among the group of line spectra toward the mirror by using at least one multi-layered film mirror or at least one X-ray filter, the multi-layered film mirror being configured to reflect the substantially one line spectrum among the group of line spectra, the X-ray filter being configured to transmit the substantially one line spectrum among the group of line spectra; and finding reflectivity of the mirror based on radiation of the substantially one line spectrum onto the mirror.

25. An optical sample X-ray testing apparatus according to claim 1, wherein the X-ray source comprises a laser plasma X-ray source.

26. A method for manufacturing a reflective mask blank, comprising:

producing a mask blank configured to be exposed with X-rays;

generating X-rays including a continuous spectrum;

cutting off visible light and UV light by using a filter;

reflecting on at least one multi-layered mirror only X-rays having a band width determined by the multi-layered mirror among the X-rays toward the mask blank; and finding reflectivity of the mask blank based on radiation of the X-rays having the band width onto the mask blank.

27. A method for manufacturing a mirror, comprising:

producing a mirror configured to be used in an X-ray optical system;

generating X-rays including a continuous spectrum;

cutting off visible light and UV light by using a filter;

reflecting on at least one multi-layered mirror only X-rays having a band width determined by the multi-layered mirror among the X-rays toward the mirror; and finding reflectivity of the mirror based on radiation of the X-rays having the band width onto the mirror.

28. An optical sample X-ray testing apparatus according to claim 5, wherein the discharge plasma X-ray source comprises a target material to generate plasma thereby radiating X-rays, the target material comprising either oxygen(O), fluorine(F), neon(Ne), lithium(Li), sodium(Na), magnesium(Mg) or aluminum(Al).

29. An-optical sample X-ray testing apparatus according to claim 20, wherein the multi-layered film mirror comprises:

a first multi-layered film mirror configured to rotate around a first axis and reflect the only X-ray having the band width determined by the first multi-layered film mirror among X-rays from the X-ray source, further comprising:

a second multi-layered film mirror configured to rotate around a second axis, move linearly and reflect the only X-ray from the first multi-layered film mirror, the second multi-layered film mirror having a periodic length same as that of the first multi-layered film mirror; and a controller configured to control a rotation of the first multi-layered film mirror and linear movements of the second multi-layered film mirror to reflect the only X-ray from the first multi-layered film mirror toward a constant direction.

30. An optical sample X-ray testing apparatus according to claim 5, wherein the line spectrum selecting devise comprises a multi-layered film mirror which is configured to reflect the substantially one line spectrum among the group of line spectra, the multi-layered film mirror having an elliptical reflective surface and being positioned such that one of two foci of the elliptical reflective surface is located at the plasma and another of two foci of the elliptical reflective surface is located at the optical surface.

31. An optical sample X-ray testing apparatus according to claim 20, wherein the X-ray source comprises a target material to generate plasma thereby radiating X-rays, the target material comprising either tungsten, tantalum, gold, tin, krypton or xenon.

* * * * *